United States Patent [19]

Rheinberger et al.

[11] Patent Number: 5,519,071
[45] Date of Patent: May 21, 1996

[54] DENTAL CEMENT

[75] Inventors: Volker Rheinberger, Vaduz, Liechtenstein; Ulrich Salz, Weissenberg, Germany

[73] Assignee: Ivoclar AG, Schaan Liechtenstein, Germany

[21] Appl. No.: 394,198

[22] Filed: Feb. 24, 1995

Related U.S. Application Data

[63] Continuation of Ser. No. 974,456, Nov. 12, 1992, abandoned.

[30] Foreign Application Priority Data

Nov. 12, 1991 [DE] Germany ............... 41 37 076.7

[51] Int. Cl.⁶ ..................... C08F 20/58; C08F 120/34
[52] U.S. Cl. ............... 523/116; 523/115; 523/118; 526/304; 526/306; 526/312; 526/316; 526/318; 526/320; 526/323.2
[58] Field of Search ..................... 523/115, 116, 523/118; 526/316, 318, 320, 323.2, 304, 306, 312

[56] References Cited

U.S. PATENT DOCUMENTS

| | | | |
|---|---|---|---|
| 4,340,529 | 7/1982 | Lee, Jr. et al. | 524/116 |
| 4,408,018 | 10/1983 | Bartman et al. | 525/304 |
| 4,408,418 | 10/1983 | Bartman et al. | 451/48 |
| 4,743,668 | 5/1988 | Fong et al. | 526/304 |
| 4,908,403 | 3/1990 | Spada et al. | 526/316 |
| 5,071,933 | 12/1991 | Muller | 523/116 |
| 5,155,252 | 10/1992 | Yamamoto et al. | 526/320 |

FOREIGN PATENT DOCUMENTS

| | | |
|---|---|---|
| 0244997 | 11/1987 | European Pat. Off. |
| 0418684 | 3/1991 | European Pat. Off. |
| 3149797 | 6/1983 | Germany |
| 2156347 | 10/1985 | United Kingdom |

*Primary Examiner*—Paul R. Michl
*Assistant Examiner*—Olga Asinovsky
*Attorney, Agent, or Firm*—Cushman Darby & Cushman

[57] ABSTRACT

The invention relates to a dental cement, a process for its preparation and its use. The cement contains a polymerisable mono or polyfunctional carbonyl compound which corresponds to one of the following general formulae:

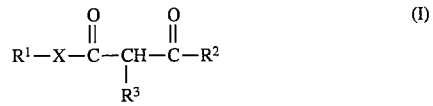

(I)

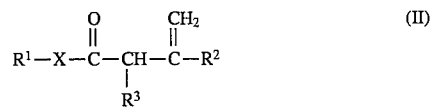

(II)

or

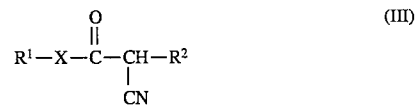 (III)

in which $R^1$ may be an alkyl, cycloalkyl, alkoxy or aryl group or a combination thereof, $R^2$ may be an alkyl, cycloalkyl, alkoxy or aryl group, a combination thereof or hydrogen, $R^3$ may be an alkyl, cycloalkyl, alkoxy or aryl group, a combination thereof or hydrogen, and X is either not present or may be O, NR, NH or S, where R may be an alkyl, cycloalkyl, alkoxy or aryl group or a combination thereof, and at least one of the groups $R^1$, $R^2$ or $R^3$ is also substituted by a group Y containing at least one polymerisable vinyl group, except for compounds containing naphthyl groups substituted with carboxylic acid anhydride functions.

8 Claims, No Drawings

DENTAL CEMENT

This is a continuation of application Ser. No. 07/974,456, filed on Nov. 12, 1992, which was abandoned upon the filing hereof.

The invention relates to a dental cement, a process for its preparation and its use.

When treating tooth material it is important to achieve a lasting and firm bond with the filling material in question. A number of adhesive systems and processes are known from the literature which bring about adhesion between dentine and composite filling materials. In principle, the prior art can be divided into three categories:

1. Processes for the surface conditioning of the dentine, particularly for the removal and consolidation of the mechanically unstable smear layer (e.g., U.S. Pat. No. 4,719,149, EP 0 287 927, U.S. Pat. No. 4,880,660 and EP 0 348 718);

2. Processes for achieving good adhesion to dentine by complexing the $Ca^{2+}$ ions on the dentine surface, phosphorus compounds (e.g., U.S. Pat. No. 4,816,495, DE-PS 34 14 163, DE-OS 31 50 285, DE-PS 28 18 068 and EP 0 132 318), carboxylic acids (e.g., U.S. Pat. No. 4,148,988, U.S. Pat. No. 3,527,737 and EP 0 325 038) or carboxylic acid derivatives (e.g., U.S. Pat. No. 4,521,550, EP 0 206 362, EP 0 377 072, EP 0 310 919 and EP 0 348 166) frequently being used.

In many cases, phosphorus compounds are also combined with carboxylic acids (e.g., EP 0 423 430). The complexing group is usually incorporated in a monomer.

3. Cements that produce a covalent bond between the collagen of the dentine and the filling composite, for example, by the use of compounds containing aldehyde groups (e.g., EP 0 141 324).

Another possibility of achieving lasting dentine adhesion was sought in carrying out controlled grafting of collagen by graft copolymerisation of methacrylic esters initiated with tri-n-butyl borane in addition to the aldehyde reaction (e.g., U.S. Pat. No. 4,830,616). Those monomers which exhibit good interpenetration as well as good bonding to the dentine substrate are generally preferred.

Combinations of 1. and 2. and 1. and 3. are common. Recently, combinations of 2. and 3. have also been claimed (e.g., U.S. Pat. No. 4,814,423).

Such systems and processes have been extensively tested in-vitro and in-vivo. At the present time, however, no cement system is known with which a sufficient adhesive capacity and at the same time a satisfactory edge seal can be obtained.

The need for improvement in the adhesion obtained with the use of the known systems and processes is shown by the fact that only adhesive types of fracture (fracture on the contact surface between the dentine and the composite) are usually observed.

The invention is based on the aim of providing a dental cement by the use of which a substantially greater adhesion of the dental materials used to the dentine or dental enamel and a better edge seal can be obtained in comparison with the known dental cements.

Said aim is achieved by a dental cement containing a polymerisable mono- or polyfunctional carbonyl compound which a) has at least one polymerisable vinyl group and b) at least one carbonyl group and in the B position to it a second carbonyl group or another functional group (i.e., a β-carbonyl structure).

The carbonyl compounds that can be used according to the invention can be subdivided into several classes:

a) monofunctional compounds i.e., monofunctional in terms of the polymerisable vinyl group and the β-carbonyl structure;

b) polyfunctional compounds, which are

α) monofunctional in terms of the polymerisable vinyl group and polyfunctional in terms of the β-carbonyl structure β) polyfunctional in terms of the polymerisable vinyl group and monofunctional in terms of the β-carbonyl structure γ) polyfunctional in terms of the polymerisable vinyl group and polyfunctional in terms of the β-carbonyl structure.

The carbonyl compounds according to the invention have one of the following general formulae:

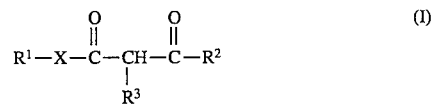

(I)

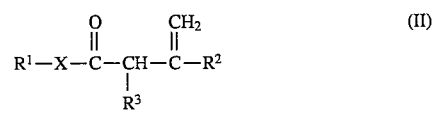

(II)

or

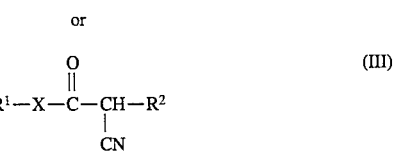

(III)

in which $R^1$ may be an alkyl, cycloalkyl, alkoxy, aryl group or a combination thereof, $R^2$ may be an alkyl, cycloalkyl, alkoxy or aryl group, a combination thereof or hydrogen, $R^3$ may be an alkyl, cycloalkyl, alkoxy or aryl group, a combination thereof or hydrogen, and X is either not present or may be O, NR, NH or S, where R may be an alkyl, cycloalkyl, alkoxy or aryl group or a combination thereof and where at least one of the groups $R^1$, $R^2$ or $R^3$ is also substituted by a group Y containing at least one polymerisable vinyl group, except for compounds containing naphthyl groups substituted with carboxylic acid anhydride functions.

The alkyl group, which may be branched or unbranched, is preferably a $C_1-C_{20}$, particularly a $C_1-C_{10}$, most preferably a $C_1-C_6$ alkyl group and the cycloalkyl group is preferably a $C_5-C_{20}$, particularly a $C_1-C_{10}$ and in particular preference a $C_5-C_6$ cycloalkyl group. The alkoxy group, whose alkyl group may be branched or unbranched, is preferably a $C_1-C_{20}$, particularly a $C_1-C_{10}$, in particular preference a $C_1-C_6$ alkoxy group and the aryl group is preferably a $C_5-C_{30}$, particularly a $C_5-C_{15}$ aryl group and in particular preference a phenyl group. Heterocyclic alkyl and aryl groups are also suitable.

For example, Y is an unsubstituted or substituted acrylic or methacrylic acid, styryl, vinyl or allyl group. Carboxyl groups which may be part of an ester, amide or thioester group, hydroxy groups, halogen atoms, alkyl groups, particularly $C_1-C_{10}$ and preferably $C_1-C_6$ alkyl groups, and/or cyanide groups are suitable as substituents.

In preferred embodiments, Y is an acrylic or methacrylic acid group, the linkage with the substituents $R^1$, $R^2$ and/or $R^3$ taking place via the carboxyl group.

The monofunctional compounds a) have, for example, the general formula:

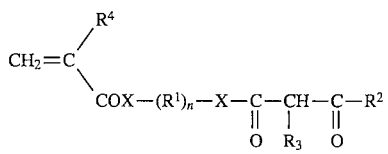 (IV)

$R^1$= alkylene, cycloalkylene, alkylenoxy, arylene,
$R^2$= alkyl, alkoxy, aryl, H,
$R^3$= alkyl, alkoxy, aryl, H,
$R^4$= alkyl, hal, H, CN,
X= no meaning or O, NR, NH, S, where R is defined as in claim 1,
n=1 and, in the case of an alkylenoxy group, up to 50, where each X may be the same or different, n is preferably equal to 1 to 10 and $R^4$ is an alkyl group or the kind mentioned above, preferably methyl or ethyl.

Inter alia, the following compounds belong to said class of compounds of the β-dicarbonyl acrylic acid derivatives:

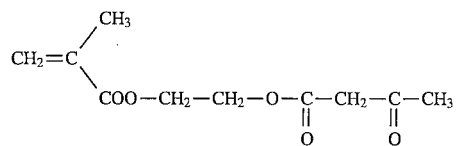 (IV,1)

(2-acetacetoxyethyl methacrylate)

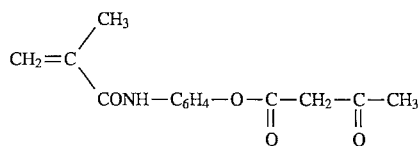 (IV,2)

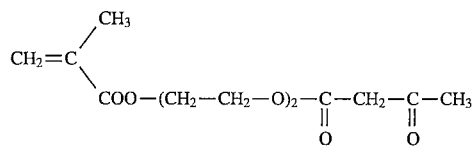 (IV,3)

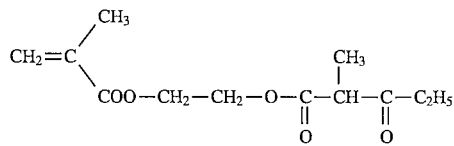 (IV,4)

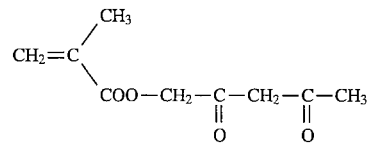 (IV,5)

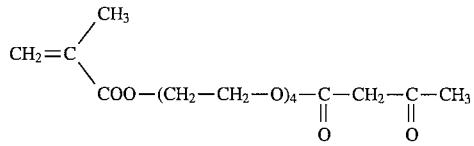 (IV,6)

(methacrylic acid-15-acetone ethyloxy-3,6,9,12-tetraoxapentadec -1-yl ester (MATP)).

Of these compounds, in particular 2-acetacetoxyethyl methacrylate (IV, 1) and the methacrylic acid-15-acetone ethyloxy-3,6,9,12 -tetraoxapentadec-1-yl ester (MATP) are preferred.

Other suitable acrylic acid derivatives have the following general formula:

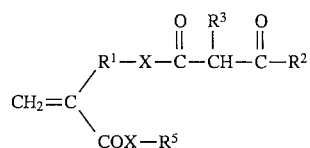 (V)

with
$R^1$= alkylene, alkenoxy, arylene,
$R^2$= alkyl, alkoxy, aryl, H,
$R^3$= alkyl, alkoxy, aryl, H,
$R^5$= alkyl, cycloalkyl, alkoxy, aryl,
X=O, NR, NH, S or is not present (R as defined above).

An example of this is the compound having the formula:

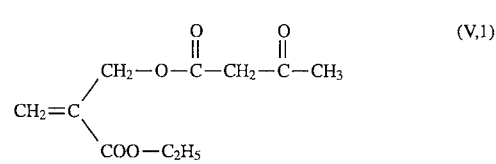 (V,1)

Compounds in which the acrylic acid group is linked to the part of the molecule bearing the β-carbonyl structure via the group $R^2$ or $R^3$ may also be used. Said compounds have the general formulae:

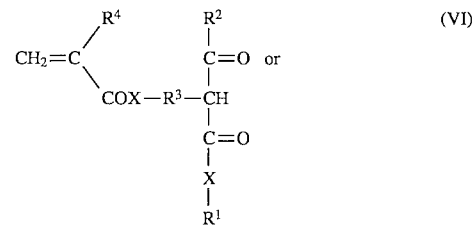 (VI)

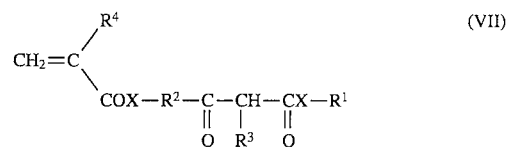 (VII)

in which the substituents $R^1$, $R^2$, $R^3$, $R^4$ and X may have the meanings given above.

Moreover, the carbonyl compounds which can be used according to the invention include those in which Y is a styryl, vinyl and allyl group instead of an acrylic acid group. Said compounds have one of the following general formulae:

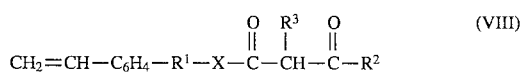 (VIII)

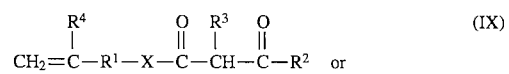 (IX)

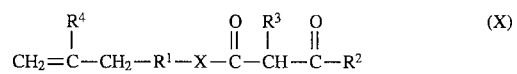 (X)

in which $R^1$, $R^2$, $R^3$, $R^4$ and X may have the meanings given and $R^1$ may have no meaning.

Here, too, the styryl, vinyl and allyl groups may be linked alternatively by one of the groups $R^2$ or $R^3$.

Examples of these are:

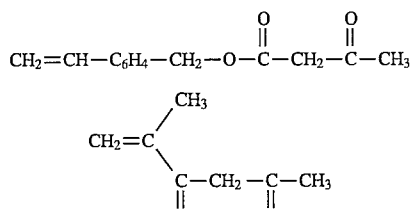
(VIII,1)
$$CH_2=CH-C_6H_4-CH_2-O-\underset{\underset{O}{\|}}{C}-CH_2-\underset{\underset{O}{\|}}{C}-CH_3$$

(IX,1)
$$CH_2=C\begin{array}{c}CH_3\\ \diagdown\\ \underset{\underset{O}{\|}}{C}-CH_2-\underset{\underset{O}{\|}}{C}-CH_3\end{array}$$

and

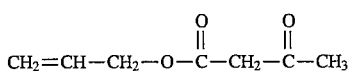
(X,1)
$$CH_2=CH-CH_2-O-\underset{\underset{O}{\|}}{C}-CH_2-\underset{\underset{O}{\|}}{C}-CH_3$$

Apart from the carbonyl compounds already mentioned which are monofunctional in terms of the β-carbonyl and the double bond function, polyfunctional β-carbonyl compounds b) are also suitable. These may be polyfunctional both in terms of the β-carbonyl structure and in terms of the polymerisable vinyl group.

α)-monofunctional in terms of the polymerisable vinyl group and polyfunctional in terms of the β-carbonyl structure:

These include, for example, compounds having the general formulae (XI)
$$CH_2=C\begin{array}{c}R^1-X-\underset{\underset{O}{\|}}{C}-\underset{\underset{R^3}{|}}{CH}-\underset{\underset{O}{\|}}{C}-R^2\\ \diagdown\\ COX-R^5\end{array}$$

in which $$R^5=R^1-X-\underset{\underset{O}{\|}}{C}-\underset{\underset{R^3}{|}}{CH}-\underset{\underset{O}{\|}}{C}-R^2,$$

and $R^1$, $R^2$, $R^3$ and X have the meanings given above, and (XII)
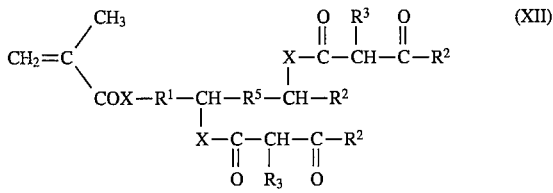

in which $R^1$, $R^2$, $R^3$ and X have the meanings given above and $R^5$ is an alkylene, cycloalkylene or arylene group of the kind mentioned above.

Examples of said compounds are:

(XII,1)
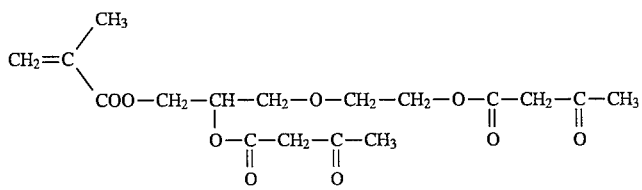

(XII,2)
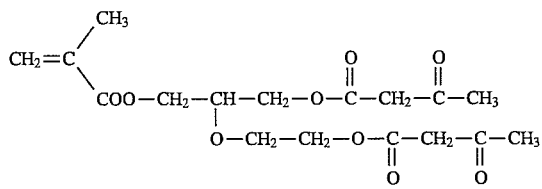

β)-polyfunctional in terms of the polymerisable vinyl group and monofunctional in terms of the β-carbonyl structure:

These include, for example, the compounds with the general formula (XIII)
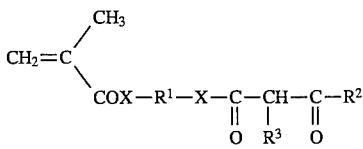

in which $R^1$, $R^2$, $R^3$ and X have the meanings given above and $R^1$, $R^2$ and/or $R^3$ contain additional polymerisable double bonds, e.g., in the form of acrylic or methacrylic acid, styryl, vinyl or allyl groups.

γ)-polyfunctional in terms of the polymerisable vinyl group and polyfunctional in terms of the β-carbonyl structure:

These may have the general formula

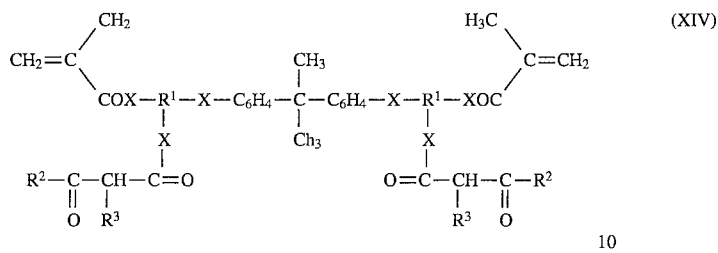

in which R¹ to R³ and X may have the meanings given. An example of this is:

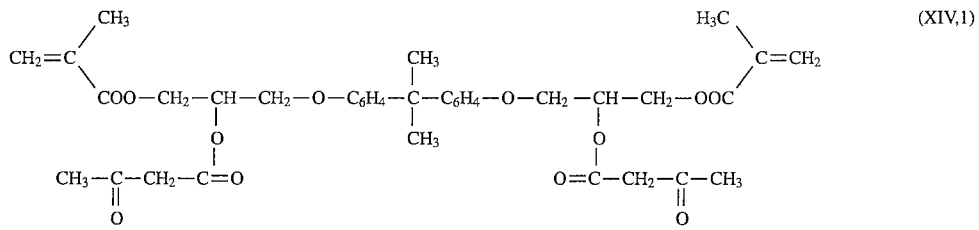

The most common process for the preparation of β-carbonyl compounds having the general formula

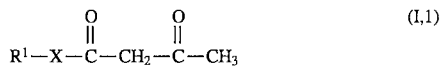

with X=O, NH, NR and S
is the reaction of a corresponding HX compound with diketen (R. J. Clemens, Chemical Review 86, 241 (1986)).

A generally applicable production specification for β-ketoesters is described in DE-OS 21 56 446, which can easily be modified, if necessary, for example in the following manner.

For example, compounds (IV, 1) and (IV,3) are obtained in a virtually quantitative yield by dissolving 1 mole of the corresponding hydroxy compound, 1 g of triethylamine and 1 g of 2,6-di-tert-butyl-p-cresol in 500 ml of absolute ethyl acetate, adding 88 g (1.05 mole) of diketen dropwise to said solution within one hour, with stirring, or adding the diketen modified according to the desired product, then heating the reaction mixture for about 2 hours under reflux, after cooling, washing first with dilute HCl and then with water and, after drying with sodium sulphate, distilling the solvent (see e.g., also DE-OS 31 49 797). MATP (IV,6) can be obtained, for example, by corresponding reaction of diketen with polyethylene glycol-200-monomethacrylate.

By analogy, p-hydroxymethacrylic acid anilide, for example, can be reacted with diketen, or hydroxyethyl methacrylate (HEMA) with

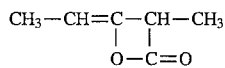

to obtain compound (IV,2) or (IV,4) and pentan-1-ol-dione-2,4 with methacrylic acid chloride or anhydride to obtain compound (IV,5).

The preparation of compounds such as (V,1) was described by T. Sato, N. Morita, H. Tanaka and T. Ota in Makromol. Chem. 191, 2599 (1990) and compounds such as (IX, 1) can be synthesised according to a specification of A. R. Despic and Dj. Kosanovic, Makromol. Chem. 29, 151 (1959).

Compounds such as (XII,1) and (XII,2) can be obtained, for example, by corresponding reaction of glycidyl methacrylate (GMA) with ethylene glycol and subsequent reaction with diketen and compounds such as (XIV, 1) by reaction of bis-GMA with diketen.

If one of the carbonyl compounds described above with at least one polymerisable vinyl group and at least one β-carbonyl structure, i.e., a carbonyl group and in the β position thereto a second carbonyl group or a functional group is used in a dental cement, substantially greater adhesion of the particular dental material to the tooth material to be treated such as dentine or dental enamel and a closer edge seal is obtained in comparison with the use of well known dental cements. The adhesive shear values achieved are three to five times greater in comparison. A cohesive type of fracture (fracture in the dentine) can frequently be observed. Apart from the preferred filling materials, moulded parts such as crowns or bridges are also possible as dental materials. The dental materials may also be metallic.

The dental cement contains about 1 to 70, particularly 1 to 50 and preferably 5 to 40% by wt. of the β-carbonyl compounds according to the invention.

The other constituents of the dental cement according to the invention are components normally used in such adhesive systems. These include, for example, PEG-200-DMA*, PEG-400-DMA*, PEG-600-DMA, PEG-1000-DMA, PEG-4000-DMA, PEG-200-monomethacrylate, PEG-400-monomethacrylate, bis-GMA, polypropylene glycol-1000-DMA, polypropylene glycol-1000-monomethacrylate, glycerol dimethacrylate, glycerol monomethacrylate, HEMA, TEG-DMA, alcohol, acetone, glutaraldehyde, camphor quinone etc. (PEG= polyethylene glycol, DMA= dimethacrylate, GMA= glycidyl methacrylate, HEMA= hydroxyethyl methacrylate and TEG= tetraethylene glycol).

Combinations with adhesion promoters already known, as described for example on pages 1 and 2 under point 1, 2 and 3 are also possible.

With regard to the mechanism of action, it is assumed that the β-carbonyl function reacts with the protein, i.e. has a substantially greater reactivity than, e.g., glutaraldehyde. Moreover, the good complexing properties may be involved in the case of the β-ketoesters and β-diketones. Moreover, the strong activation of the α-methylene group could be involved.

It has proved to be advantageous to treat dentine with a primer before applying the cement according to the invention. For example, Syntac® primer has proved to be a suitable primer.

In the examples 1 to 6 below, dental cement formulations according to the invention are described which contain 2-acetacetoxyethyl methacrylate (1 to 3) and MATP. Examples 7 and 8 are comparative examples and demonstrate the superiority of the cement formulations according to the invention in comparison with well known cement formulations.

The dental cement formulations used were prepared by adding the individual constituents, with stirring, to the charge of solvent mixture. Stirring was then continued until a homogeneous, clear solution was obtained. The adhesive shear values determined are given for the respective formulations.

In order to determine the adhesive shear values, the primer was first applied in a thin layer to surface-ground (1000 abrasive paper) dentine surfaces, dried with an air blower, of extracted, embedded teeth. After a contact time of 20 seconds, the primer was dried briefly with an air blower and the cement was then applied again in a thin layer and blown lightly. After the application and curing of a light-curing bonding (Heliobond® from Vivadent), a special, divisible Teflon mould (d=4 mm, h=6 mm) was fixed to the dentine surface with a special fixing device (fixing device comparable with that described by D. H. Retief, J. D. Gross, E. L. Bradley and F. R. Denys in Dental Materials 2, 72 (1986). A light-curing filling composite (Heliomolar, Tetras) was then polymerised in layers onto the dentine surface in a defined volume and with a defined adhesive surface.

The adhesive shear values were determined either directly after preparation of the test specimens (1 minute and 5 minutes) or after a correspondingly long period of storage in distilled water at 37° C.

When the dental cements according to the invention were used, very high adhesion values were achieved almost immediately after polymerisation of the filling composite. This is very important for clinical application because very high initial adhesion counteracts the polymerisation shrinkage of the filling material and a close edge seal with the filling can thus be obtained. Commercial dentine cements such as Scotchbond® and Gluma® exhibit clearly measurable dentine adhesion only after 24 hours' storage in water (see examples 7 and 8).

It could also be shown, however, that a lasting cohesive bond can be obtained with the system according to the invention.

The determination of the adhesion values was carried out using a special shearing device as described in a comparative manner, e.g., by K. Ludwig, Dental Labor 37, (5), 757 (1989) (material testing apparatus Zwick 1455/speed of movement 0.5 mm/min).

| Syntac ® primer | |
|---|---|
| Maleic acid | 4% by wt. |
| TEG-DMA* | 25% by wt. |
| Water | 30% by wt. |
| Acetone | 41% by wt. |

*TEG-DMA = tetraethylene glycol-dimethacrylate

EXAMPLE 1

(Combination of 2-acetacetoxyethyl methacrylate with polyethylene glycol dimethacrylate (PEG-DMA))

| | | |
|---|---|---|
| 1. | a) 2-Acetacetoxyethyl methacrylate | 5% by wt. |
| | PEG-1000-DMA | 30% by wt. |
| | Ethanol/water (1:1) | 65% by wt. |
| | Dentine adhesion (24 h/H$_2$O/37° C.): | |
| | 21 ± 5 MPa (cohesive fractures in 2 out of 6 samples) | |
| | Dentine adhesion (6 months/H$_2$O/37° C.): | |
| | 19 ± 4 MPa (cohesive fractures in 3 out of 6 samples) | |
| | Dentine adhesion (5 minutes): 11 ± 3 MPa | |
| | b) 2-Acetacetoxyethyl methacrylate | 10% by wt. |
| | PEG-1000-DMA | 30% by wt. |
| | Ethanol/water (1:1) | 60% by wt. |
| | Dentine adhesion (24 h/H$_2$O/37° C.): | |
| | 18 ± 6 MPa (cohesive fractures in 4 out of 6 samples) | |
| | Dentine adhesion (6 months/H$_2$O/37° C.): | |
| | 17 ± 5 MPa (cohesive fractures in 4 out of 6 samples) | |

EXAMPLE 2

(Combination of 2-acetacetoxyethyl methacrylate with glutaraldehyde)

| | | |
|---|---|---|
| 2. | a) 2-Acetacetoxyethyl methacrylate | 10% by wt. |
| | Glutaraldehyde (50%) | 40% by wt. |
| | Ethanol/water (2:1) | 50% by wt. |
| | Dentine adhesion (24 h/H$_2$O/37° C.): | |
| | 17 ± 4 MPa (cohesive fractures in 4 out of 6 samples) | |
| | Dentine adhesion (6 months/H$_2$O/37° C.): | |
| | 18 ± 5 MPa (cohesive fractures in 5 out of 6 samples) | |
| | Dentine adhesion (5 minutes): 12 ± 2 MPa | |
| | Dentine adhesion (1 minute): 9 ± 3 MPa | |
| | b) 2-Acetacetoxyethyl methacrylate | 10% by wt. |
| | Glutaraldehyde (50%) | 60% by wt. |
| | Ethanol/water (2:1) | 30% by wt. |
| | Dentine adhesion (24 h/H$_2$O/37° C.): | |
| | 16 ± 5 MPa (cohesive fractures in 3 out of 6 samples) | |
| | c) 2-Acetacetoxyethyl methacrylate | 5% by wt. |
| | Glutaraldehyde (50%) | 60% by wt. |
| | Ethanol/water (2:1) | 35% by wt. |
| | Dentine adhesion (24 h/H$_2$O/37° C.): | |
| | 18 ± 6 MPa (cohesive fractures in 3 out of 6 samples) | |

EXAMPLE 3

(Combination of 2-acetacetoxyethyl methacrylate with hydroxyethyl methacrylate HEMA)

| | | |
|---|---|---|
| 3. | a) 2-Acetacetoxyethyl methacrylate | 10% by wt. |
| | HEMA | 30% by wt. |
| | Ethanol/water (1:1) | 60% by wt. |
| | Dentine adhesion (24 h/H$_2$O/37° C.): | |
| | 18 ± 5 MPa (cohesive fracture in 1 out of 6 samples) | |
| | Dentine adhesion (6 months/H$_2$O/37° C.): | |
| | 15 ± 3 MPa (cohesive fractures in 2 out of 6 samples) | |
| | b) 2-Acetacetoxyethyl methacrylate | 20% by wt. |
| | HEMA | 20% by wt. |
| | Ethanol/water (1:1) | 60% by wt. |
| | Dentine adhesion (24 h/H$_2$O/37° C.): | |
| | 13 ± 6 MPa (cohesive fractures in 2 out 6 samples) | |
| | c) 2-Acetacetoxyethyl methacrylate | 40% by wt. |
| | HEMA | 20% by wt. |
| | Ethanol/water (1:1) | 40% by wt. |
| | Dentine adhesion (24 h/H$_2$O/37° C.): | |
| | 15 ± 6 MPa (cohesive fractures in 2 out of | |

EXAMPLE 4

(Combination of MATP with PEG-1000-DMA)

| 1. | a) MATP | 5% by wt. |
|---|---|---|
| | PEG-1000-DMA | 30% by wt. |
| | Ethanol/water (1:1) | 65% by wt. |
| | Dentine adhesion (24 h/H$_2$O/37° C.): | |
| | 35 ± 6 MPa (all fractures cohesive) | |
| | b) MATP | 10% by wt. |
| | PEG-1000-DMA | 30% by wt. |
| | Ethanol/water (1:1) | 60% by wt. |
| | Dentine adhesion (24 h/H$_2$O/37° C.): | |
| | 17 ± 9 MPa (80% of the fractures cohesive) | |
| 2. | MATP | 10% by wt. |
| | Glutaraldehyde (50%) | 30% by wt. |
| | Ethanol/water (1:1) | 60% by wt. |
| | Dentine adhesion (24 h/H$_2$O/37° C.): | |
| | 34 ± 8 MPa (all fractures cohesive) | |
| 3. | MATP | 10% by wt. |
| | HEMA | 30% by wt. |
| | Ethanol/water (1:1) | 60% by wt. |
| | Dentine adhesion (24 h/H$_2$O/37° C.): | |
| | 33 ± 11 MPa (all fractures cohesive) | |

EXAMPLE 5

(Enamel adhesion)

The enamel was ground with 1000 sand paper.

| 1. | Adhesive was applied directly to the enamel. | |
|---|---|---|
| | MATP | 10% by wt. |
| | HEMA | 30% by wt. |
| | Ethanol/water (1:1) | 60% by wt. |
| | Enamel adhesion (24 h/H$_2$O/37° C.): | |
| | 3.7 ± 2.7 MPa. | |
| 2. | Syntac primer was applied initially to the enamel. | |
| | a) MATP | 5% by wt. |
| | PEG-1000-DMA | 30% by wt. |
| | Ethanol/water (1:1) | 65% by wt. |
| | Enamel adhesion (24 h/H$_2$O/37° C.): | |
| | 22.3 ± 4.9 MPa | |
| | b) MATP | 10% by wt. |
| | PEG-1000-DMA | 30% by wt. |
| | Ethanol/water (1:1) | 60% by wt. |
| | Enamel adhesion (24 h/H$_2$O/37° C.): | |
| | 24.5 ± 5.3 MPa | |
| | c) MATP | 10% by wt. |
| | Glutaraldehyde (50%) | 30% by wt. |
| | Ethanol/water (1:1) | 60% by wt. |
| | Enamel adhesion (24 h/H$_2$O/37° C.): | |
| | 26.9 ± 10.7 MPa | |
| | d) MATP | 10% by wt. |
| | HEMA | 30% by wt. |
| | Ethanol/water (1:1) | 60% by wt. |
| | Enamel adhesion (24 h/H$_2$O/37° C.): | |
| | 22.2 ± 15.1 MPa | |

EXAMPLE 6

(Metal adhesion)

The adhesion to sand-blasted Wiron 88 (Ni/Cr/Mo alloy made by Bego) was tested in the first instance.

| 1. | a) Acetoacetoxyethyl-MMA | 20.0% by wt. |
|---|---|---|
| | bis-GMA | 10.0% by wt. |
| | Tetraethylene glycol-DMA | 20.0% by wt. |
| | Acetone | 49.6% by wt. |
| | Camphor quinone | 0.15% by wt. |
| | N-cyanoethyl-N-methylaniline | 0.25% by wt. |

With the example, a thin layer of said solution was applied to the metal surface and left to dry. Opaque powder (Ivoclar) was then mixed with said solution and applied thinly. After drying, the surface is then exposed for 60 sec. with the Heliomat. Helioprogress is then applied and polymerised for 3×40 sec.

Metal adhesion (24h/H$_2$O/37° C.): 14.9±1.7 MPa

| | b) Acetoacetoxyethyl-MMA | 8.0% by wt. |
|---|---|---|
| | bis-GMA | 4.0% by wt. |
| | Tetraethylene glycol-DMA | 8.0% by wt. |
| | Acetone | 79.8% by wt. |
| | Camphor quinone | 0.07% by wt. |
| | Cyanoethylmethyl aniline | 0.13% by wt. |

Procedure as described above.

Metal adhesion (24h/H$_2$O/27° C.): 16.3±1.8 MPa

For comparison, metal adhesion of 16.1±2.7 MPa was obtained with the existing Spektra-Link (Ivoclar).

The given values for adhesion are to be regarded as relative values and not absolute values since, in a comparison of the results of several test series of identical experiments, the relationships are the same but the values determined may differ from one another in the comparison of the test series amongst themselves. In view of the diverse quality of the extracted teeth used, more cohesive fractures are observed in many cases with somewhat lower adhesion values.

In comparison with the dental cements known hitherto, considerably improved adhesion values are obtained on the whole, which leads to a smaller number of adhesive fractures and a greater number of cohesive fractures.

When the dental cement according to the invention used in the formulations described above is replaced by one of the well-known cements Syntac®, Gluma®, Scotchbond® 2, Tenure®, dentine adhesion values in the region of 5 to 8 MPa are measured.

EXAMPLE 7 (COMPARATIVE EXAMPLE)

Scotchbond® 2 (from 3M) was used in this example.

Primer=2.5% maleic acid 58.5% hydroxyethyl methacrylate (HEMA) in water

Cement=62.5% bis-GMA 37.5% hydroxyethyl methacrylate (HEMA) Photoinitiators (according to G. H. Johnson, V. Powell and G. E. Gordon; Dentine Bonding Systems: A Review of Current Products and Techniques; J. Am. Dent. Assoc. 122, 34 (1991)).

Primer and cement were used in accordance with the manufacturers' instructions.

Dentine adhesion (24h/H$_2$O/37° C.): 8±2 MPa*

Dentine adhesion (1 minute): 2±2 MPa*

EXAMPLE 8 (COMPARATIVE EXAMPLE)

Gluma ® (from Bayer) was used in this example.

Dentine cleaner=16% EDTA solution

Primer=35% hydroxyethyl methacrylate (HEMA) 5% glutaraldehyde in water

Sealant=bis-GMA
(according to G. H. Johnson et al.)

Dentine cleaner, primer and sealant were used in accordance with the manufacturers' instructions.

Dentine adhesion (24h/$H_2O$/37° C.): 7±3 MPa*

Dentine adhesion (1 minute): 3±2 MPa*

*Only adhesive fractures were observed.

We claim:

1. Dental cement, comprising:

about 1 to 70 wt. % of a polymerisable mono or polyfunctional carbonyl compound which has a) at least one polymerisable vinyl group and b) at least one carbonyl group and in the β position thereto a second carbonyl group or another functional group, the carbonyl compound corresponding to one of the following general formulae, (II), (III) and (IV):

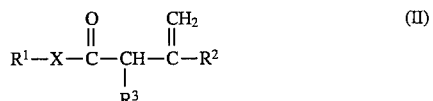

or

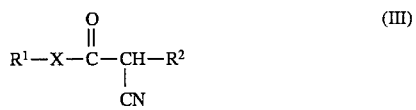

in which $R^1$ may be an alkyl, cycloalkyl, alkoxy or aryl group or a combination thereof, $R^2$ may be an alkyl, cycloalkyl, or aryl group, a combination thereof or hydrogen, $R^3$ may be an alkyl, cycloalkyl, alkoxy or aryl group, a combination thereof or hydrogen, and X is either not present or may be O, NR, NH or S, where R may be an alkyl, cycloalkyl, alkoxy or aryl group or a combination thereof, and at least one of the groups $R^1$, $R^2$ or $R^3$ is also substituted by a group Y containing at least one polymerisable vinyl group, except for compounds that contain naphthyl groups substituted with carboxylic acid anhydride functions; or said carbonyl compound corresponds to the following formula (IV):

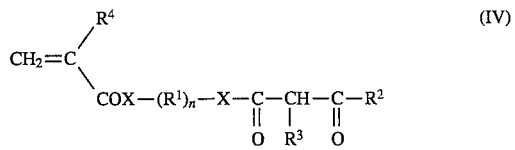

in which $R^1$, when substituted with Y, is alkylene, cycloalkylene, alkylenoxy, or arylene, $R^2$ = alkyl, aryl, or H, $R^3$ = alkyl, alkoxy, aryl, or H, $R^4$ = alkyl, hal, H, or CN, X = NR, NH, or S, n=1 and, in the case of an alkylenoxy group, up to 50, where X in each case may be the same or different; and said dental cement includes at least one component selected from the group consisting of polyethylene glycol-400-dimethacrylate, polyethylene glycol-600-dimethacrylate, polyethylene glycol-1000-dimethacrylate, polyethylene glycol -4000-dimethacrylate, polyethylene glycol-200-monomethacrylate, polyethylene glycol-400-monomethacrylate, polypropylene glycol -1000-dimethacrylate, polypropylene glycol-1000-monomethacrylate, glycerol dimethacrylate, glycerol monomethacrylate, hydroxyethyl, methacrylate, glutaraldehyde and tetraethylene glycol dimethacrylate.

2. Dental cement according to claim 1, characterised in that Y is an unsubstituted or substituted acrylic acid or methacrylic acid group, styryl, vinyl or allyl group.

3. Dental material according to claim 1, characterised in that Y is substituted by carboxyl groups which may be part of an ester, amide or thioester group, hydroxy groups, alkyl groups, halogen atoms and/or cyanide groups.

4. Dental cement according to claim 1, characterised in that the carbonyl compound is:

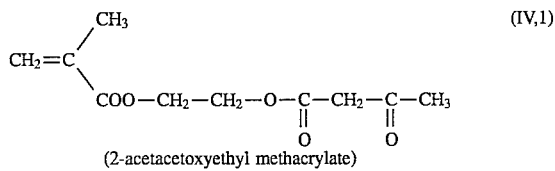

(2-acetacetoxyethyl methacrylate)

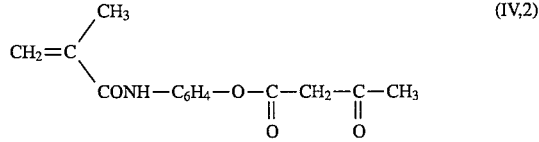

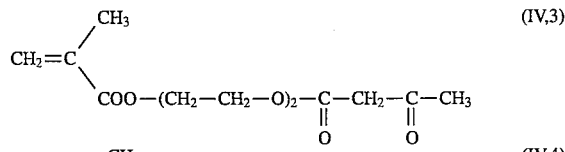

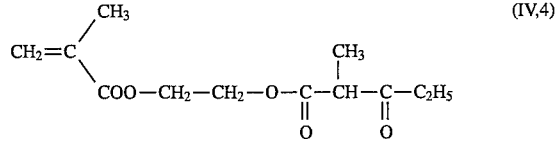

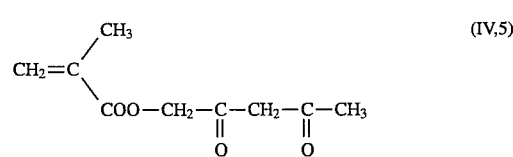

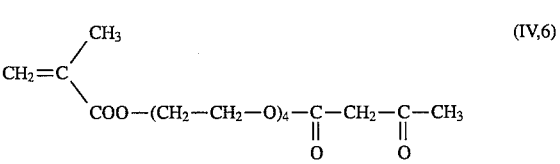

5. Dental cement according to claim 1, characterised in that the carbonyl compound has several polymerisable vinyl groups and/or several carbonyl groups with a second carbonyl group or another functional group in the B position thereto.

6. Dental cement according to claim 1, characterised in that it contains 1 to 50 and preferably 5 to 40% by wt. of the carbonyl compound.

7. Process for the preparation of a dental cement according to claim 1 comprising the steps of adding with stirring the carbonyl compound and the at least one component according to claim 1 with the other cement constituents, to a charge of solvent mixture and then stirring until such time as a homogeneous, clear solution is obtained.

8. Method of bonding a tooth material to a dental material by applying the dental cement of claim 1, to result in a lasting and firm bond.

* * * * *